United States Patent
Erickson

[11] Patent Number: 6,149,812
[45] Date of Patent: Nov. 21, 2000

[54] DENTAL ENVIRONMENTAL FILTER FOR HEAVY METALS AND MERCURY HYGIENE

[76] Inventor: Roger T. Erickson, 1010 Broncho Rd., Pebble Beach, Calif. 93953

[21] Appl. No.: 09/176,812

[22] Filed: Oct. 22, 1998

[51] Int. Cl.[7] ............................. A61C 17/06; B01D 21/00
[52] U.S. Cl. ...................... 210/521; 210/532.1; 433/92; 433/97
[58] Field of Search .................. 210/521, 532.1, 210/254, 513; 433/92, 97

[56] References Cited

U.S. PATENT DOCUMENTS

| | | | |
|---|---|---|---|
| 54,414 | 5/1866 | Sangster | 210/521 |
| 1,032,879 | 7/1912 | Carlton et al. | 210/532.1 |
| 2,467,547 | 4/1949 | Birnbaum | 210/532.1 |
| 4,326,952 | 4/1982 | Blake | 210/521 |
| 4,385,891 | 5/1983 | Ligotti | 433/92 |
| 4,761,235 | 8/1988 | Haentjens | 210/532.1 |
| 4,957,621 | 9/1990 | Rohloff | 210/521 |
| 5,114,578 | 5/1992 | Sundström | 210/521 |

Primary Examiner—Christopher Upton
Attorney, Agent, or Firm—Robin Chiang; Barbara Rae-Venter; Rae Venter Law Group, P.C.

[57] ABSTRACT

A dental environmental filter is provided for the collection of heavy metals and other particles during dental or other procedures. The dental environmental filter incorporates a manifold with an inlet conduit and an outlet conduit, with an adjustable control handle on the top of the manifold and a baffle plate in the inside of the manifold. The manifold is sealed to the top opening of a collection chamber. During procedures which require withdrawal of fluids, the control handle and baffle plate are adjusted to a fluids mode which connects a internal adjustable conduit, which transverses through the baffle plate, with the lumen of the inlet and outlet conduits to form a continuous lumen with which to withdraw fluids through. During procedures which require the withdrawal of heavy metals or other particles, the control handle and baffle plate are adjusted to a solids mode which orients the baffle plate to face the both the lumen of the inlet and outlet conduits. Heavy metals and other particles drawn by a vacuum are deflected by the baffle plate and fall by gravity into the collection chamber. The collection chamber is removable and can be covered by a lid.

8 Claims, 4 Drawing Sheets

DENTAL ENVIRONMENTAL FILTER FOR HEAVY METALS AND MERCURY HYGIENE

FIELD OF THE INVENTION

This invention relates to an environmental filter for the filtration, collection and isolation of finite heavy metals used in the field of dentistry, specifically for recycling purposes of silver, gold and mercury. Also of great importance is the isolation from the environment of mercury which is a toxic element.

BACKGROUND

The dental filter currently used in dental offices is a simple plastic perforated screen which is located in the vacuum conduit line leading to the sewer line. This filter fails to accomplish all needed functions of a dental filter.

The dentist and dental assistant sit on adjustable stools on opposite sides of the reclined contour dental chair near the patient's head. The dentist prepares the patient's teeth for restoration with a high speed turbine handpiece (drill) to remove decay and shape the tooth to be restored. During some parts of the procedure a water spray is used to wash the tooth and the operating field (washed field technique). Tooth structure particles and/or existing old defective silver-mercury amalgam or gold restorations are aspirated from the operating field of the oral cavity. This aspiration is done by the dental assistant using a vacuum tip attached to a conventional flexible vacuum tubing. The solids, water spray and oral fluids are deposited via the vacuum tubing into the perforated plastic screen and from there are deposited into the sewer line.

The dental filter currently in use suffers from many disadvantages and fails completely to accomplish the function of a dental filter:

(a) The particles of the silver-mercury amalgam, gold and tooth structure produced by the drilling procedure are reduced to a very small particle size. These small particles escape through the perforations of the plastic screen and are lost into the sewer system.

(b) Mercury, also a heavy metal, is a liquid at room temperature and in its free state is a very toxic substance. Therefore, if liquid mercury is accidentally spilled on operating surfaces or on the floor, it can be easily aspirated up by the vacuum tip. However, it easily escapes through the plastic screen perforations. The mercury then enters the sewer lines and ultimately into the environment.

(c) Another defective feature in the above described filter screen is that the aspirated water and oral fluids are aspirated together along with the solid materials being removed from the oral cavity.

(d) The perforated screen type filter does not allow for the separation of the water fluid phase from the solids phase during the dental procedure.

SUMMARY OF THE INVENTION

The invention is an environmental filter that functions as a filter by using air flow created by a conventional vacuum system, a manifold, a baffle plate, a collection chamber, and the force of gravity. The invention allows for the separation of the heavy metals (solids mode) from the water and oral fluids (fluids mode). This is accomplished simply by turning a control handle to the proper setting, i.e., either the fluids mode or solids mode. In the solids mode, heavy metals and other particles drawn in by vacuum strike the baffle plate, and by the effect of gravity fall into the collection chamber. When the chamber is sufficiently filled, the chamber is unscrewed from the manifold and a lid is screwed onto the chamber. This seals the chamber for storage of the collected heavy metal materials. A new collection chamber is then screwed into its place in the manifold. In the fluids mode (FIGS. 3, 3A), the water and oral fluids bypass the solids collection jar. The fluids flow directly through the inner conduit, located inside the baffle plate, which has been turned 90° and the fluids flow directly into the sewage line.

The invention keeps heavy metals collected in a dry state. This is important for storage while awaiting to be sent out for recycling of the recovered heavy metals. The invention captures mercury for recycling and prevents the mercury, which is toxic, from contaminating the environment. All parts of this invention can be composed of plastic which will not allow for corrosion of the parts. The invention can be easily manufactured by any plastics company which manufactures plastic parts or plastic implements. The invention can be is easily disassembled for cleaning purposes by the dental staff members.

DESCRIPTION OF THE SPECIFIC EMBODIMENTS

Figure 1:
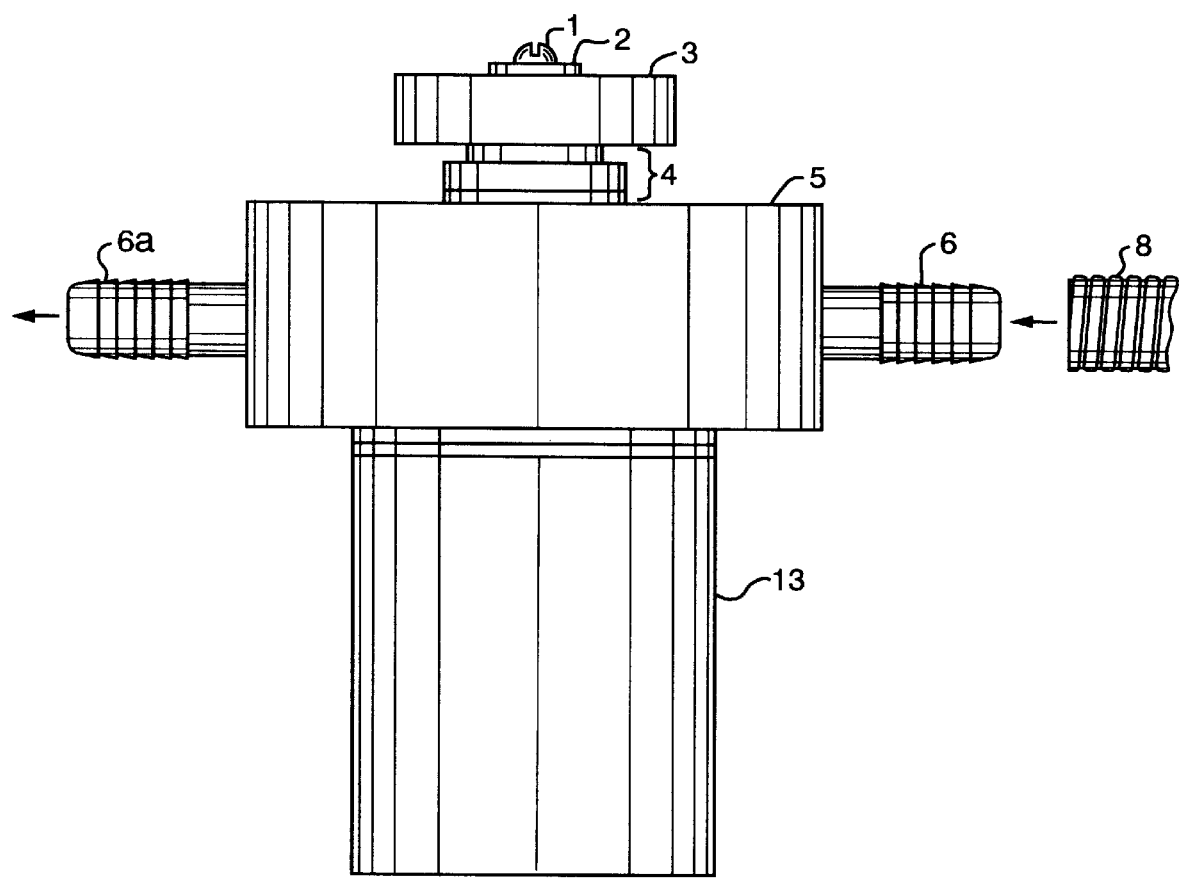
FIG. 1 is a side view of the environmental filter.
Figure 2:
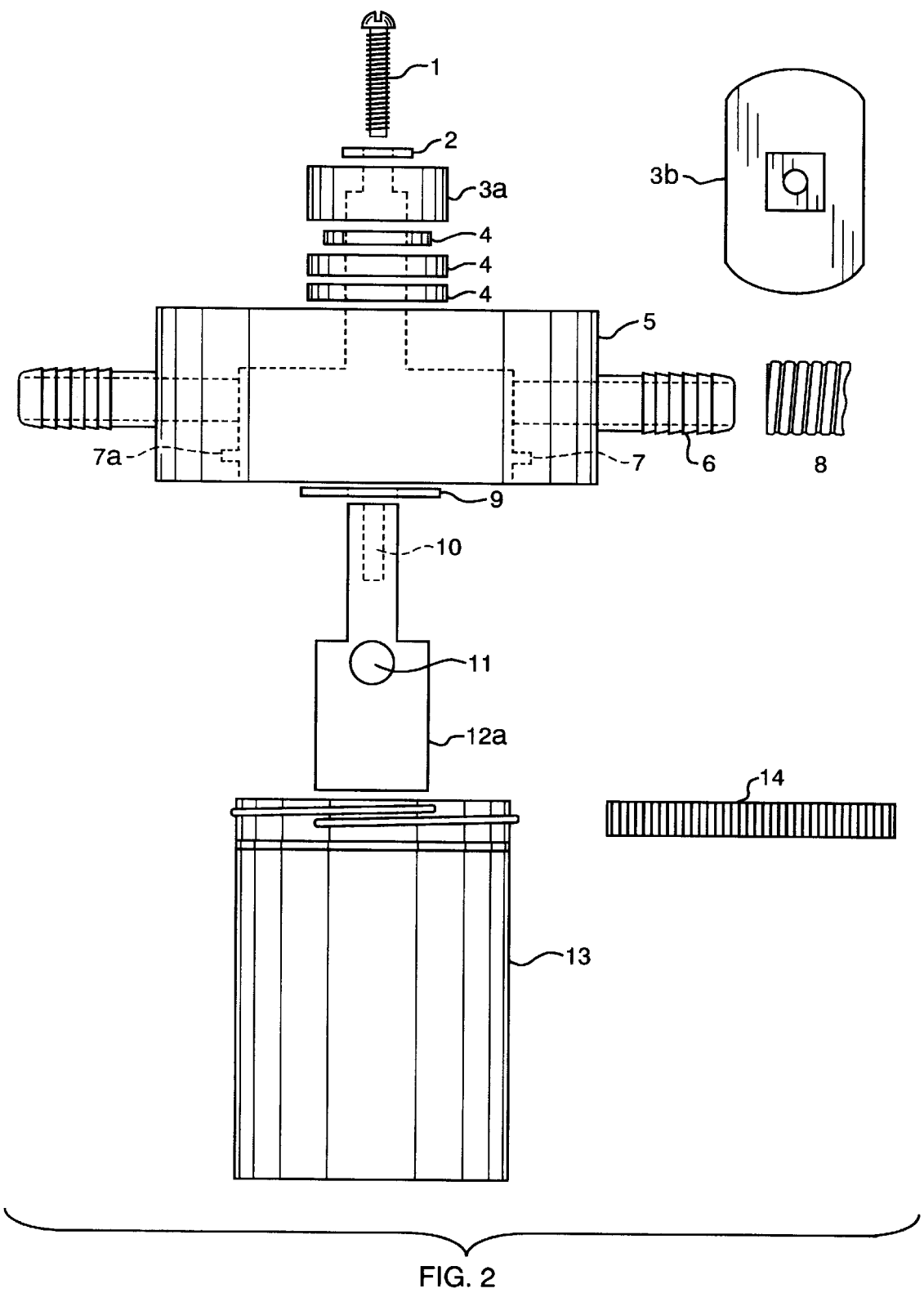
FIG. 2 is an explosion side view of all the parts of the environmental filter.

An embodiment of the invention is shown in FIGS. 1 and 2. A screw 1 holds the control handle 3 in place which screws into the extended neck threads 10 of the conduit/baffle partition. There is a plastic washer 2 between the screw 1 and the control handle 3. The control handle 3 can be positioned in the fluids mode 3 or the solids mode 3A. Washers 4A, 4B, 4C between the control handle 3 and the top of the manifold 5 elevate the control handle 3 for turning convenience and to reduce friction when turning the control handle 3. The manifold 5 provides outlets through which vacuum air, fluids and solid materials are distributed. The manifold 5 coordinates and holds together the principal parts of the invention. There are the entry external conduit 6 and exit external conduit 6A, to which conventional vacuum tubing 8 fasten. The entry external conduit 6 and exit external conduit 6A direct the directions of the incoming air 18 and the outgoing air 18A. Female threads 7, 7A in the manifold 5 join with the male threads 17 of the collection chamber 13. The washer 9 between the manifold 5 and the baffle plate/internal conduit portion assist in the free turning of the internal adjustable conduit (lumen) 11 and the baffle plate 12. The female threads 10 in the neck (top) portion of the internal conduit/baffle plate receive the screw 1. In the fluids mode, the internal adjustable conduit (lumen) 11A located in the baffle plate 12 is turned 90° clockwise from the solids mode orientation. In the fluids mode, the adjustable internal conduit (lumen) 11A forms a continuous lumen with the entry internal conduit (lumen) 16 and the exit internal conduit (lumen) 16A, located in the manifold 5 portion. In the solids mode, the internal adjustable conduit (lumen) 11 located in the baffle plate 12A is turned 90° counter-clockwise from the fluids mode orientation. The baffle plate 12A, when in the solids mode orientation, deflects heavy metals into collection chamber 13. Lid 14 is for covering the heavy metals collection chamber 13. A stop 15 is located inside the manifold 5 to control the orientation of the internal adjustable conduit 11A for the fluids mode. A stop 15A is located inside the manifold 5 to control the orientation of the adjustable baffle plate 12A for the fluids mode. The entry internal conduit (lumen) 16 forms a continuous lumen with the entry external conduit 6. The exit internal conduit (lumen) 16A forms a continuous lumen with the exit external conduit 6A. Arrow 18 depicts the direction of vacuum flow during the solids mode. Arrow 18A depicts the direction of vacuum air flow and fluid flow during the fluids mode. The vertical arrow 19 depicts the direction of the heavy metals falling toward the bottom of the collection chamber 13 due to the collision of the heavy metals particles with the baffle plate 12A and due to the effect of gravity on the particles.

Conventional plastic vacuum tubing 8 is fastened to entry external conduit 6 and exit external conduit 6A, which are located entering and exiting each side of a manifold 5. The exit external conduit 6A is connected to a conventional vacuum source via conventional vacuum tubing 8 and exits into the sewage system. The assembled environmental filter is fastened to a conventional dental light post using a conventional plastic strap.

Figure 3:
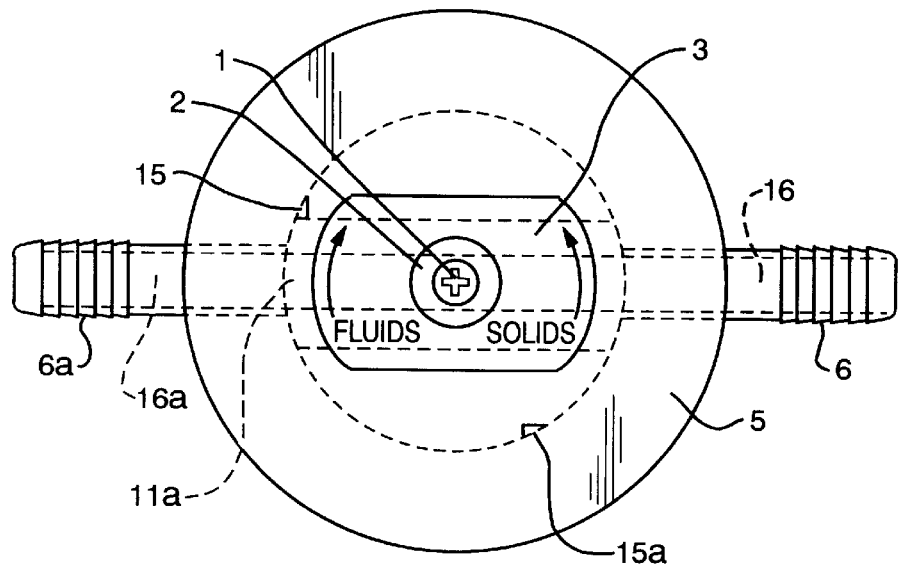
FIG. 3 is a top view, looking down on the top of the environmental filter with the control handle in fluids mode.
Figure 3A:
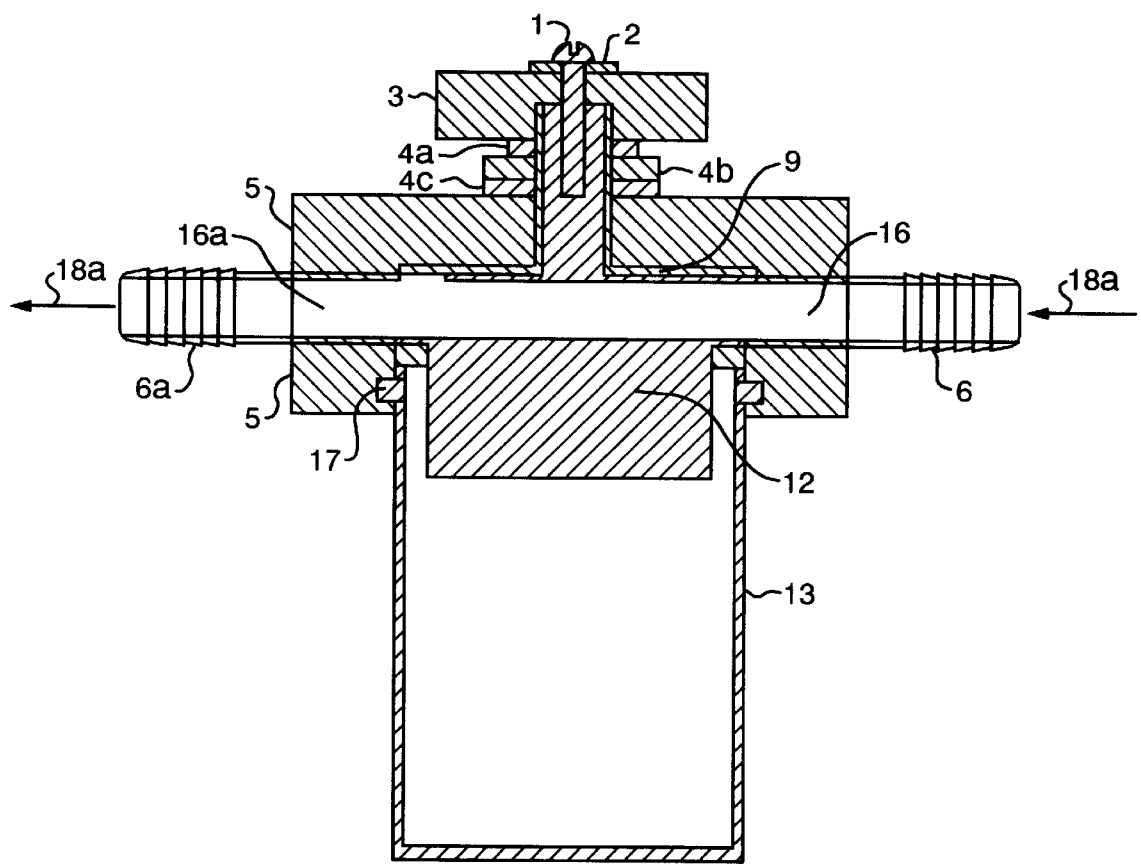
FIG. 3A is a side sectional of the environmental filter view in the fluids mode.

The operation of the environmental filter is done by the chairside dental assistant while assisting the dentist in the dental procedures. The control handle 3 is turned 90° to the fluids mode. In the fluids mode no heavy metals are being collected. The fluids mode allows for the aspiration of water spray used during drilling procedures on teeth (washed field technique) and the aspiration of oral fluids such as saliva or blood during oral surgery procedures. In the fluids mode (see FIGS. 3 and 3A), fluids move by conventional vacuum pressure through the dental assistant's conventional aspirating tip, conventional vacuum tubing 8, through the entry external conduit 6, through the entry internal conduit 16, through the adjustable internal conduit 11A, through the exit internal conduit 16A, through the exit external conduit 6A, and exiting through conventional vacuum tubing 8, finally emptying into the sewer line. Thus, during the fluids mode, air and fluids drawn the vacuum bypasses the heavy metals collection chamber 13, and deposits the fluids directly into the sewage line.

Figure 4:
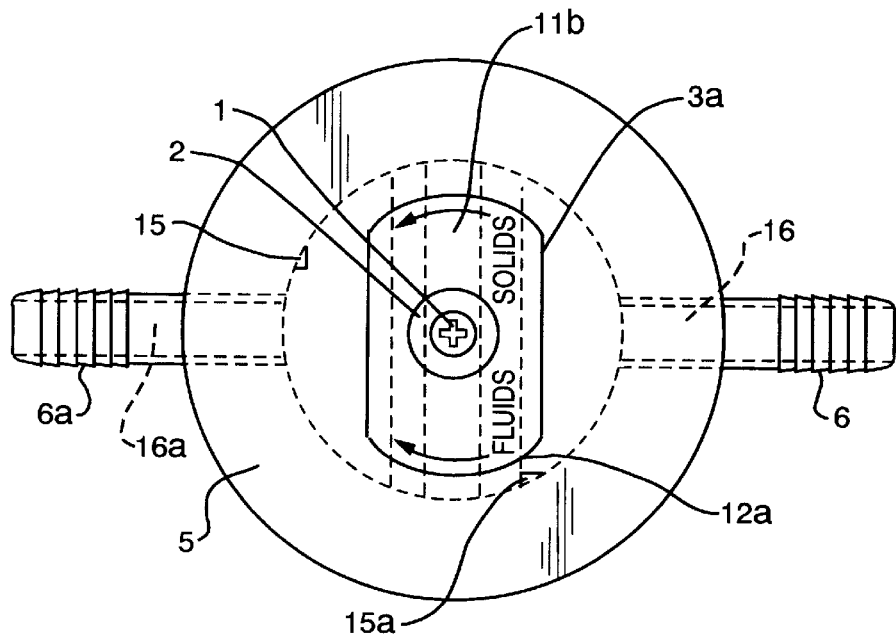
FIG. 4 is a top view, looking down on the top of the environmental filter with the control handle in the solids mode.
Figure 4A:
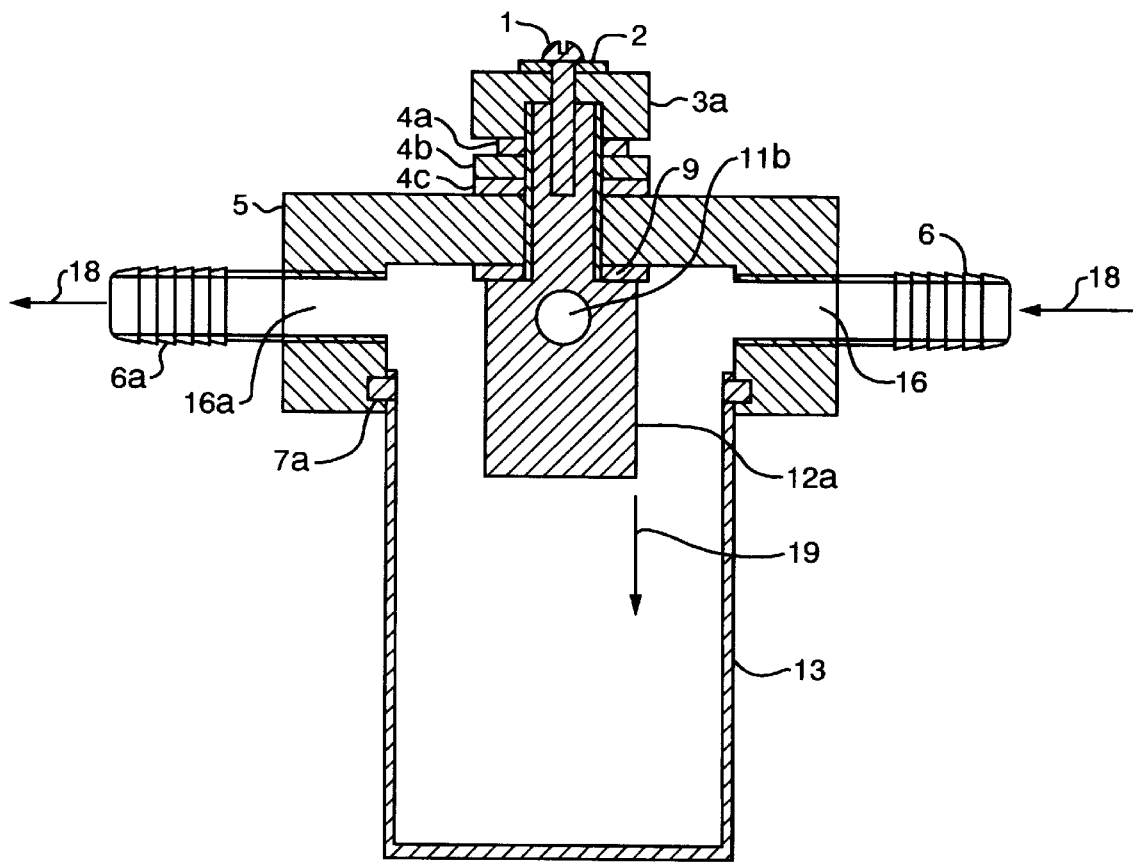
FIG. 4A is a sectional view of the environmental filter in the solids mode.

The solids mode is used during the collection phase of the heavy metals and other solid materials. The control handle 3A is turned 90° to the solids mode. The solid materials are old, defective silver-mercury amalgam or gold restorations which are being removed during the preparation of teeth for new restorations. The solid materials also include the silver-mercury amalgam carvings resulting from shaping new silver-mercury amalgam fillings. In the solids mode (see FIGS. 4 and 4A), as the dentist carves the anatomy of the still malleable silver-mercury amalgam, the dental assistant aspirates amalgam carvings (i.e., the heavy metals) by conventional vacuum pressure through the dental assistant's conventional aspirating tip, conventional vacuum tubing 8, through the entry external conduit 6, and through the entry internal conduit 16. The heavy metals then strike the baffle plate 12A from where the heavy metal particles drop in direction indicated by the arrow 19, due to gravity, into the heavy metals collection chamber 13. Any excess heavy metal restorative materials, or accidentally spilled mercury on operating surfaces or the floor, can be aspirated into the heavy metals collection chamber 13 in the same manner. Thus, these heavy metal materials can be collected for the purpose of recycling finite heavy metals. Mercury, which is very toxic in its free state, is prevented from entering and contaminating the environment.

When the heavy metals collection chamber 13 has been sufficiently filled with heavy metals, the jar is unscrewed form the manifold 5 and sealed with a lid 14 for storage and recycling of the heavy metals. An empty heavy metals collection chamber 13 is then screwed into place in manifold 5.

Further objects and advantages of the invention will become apparent from a consideration of the drawings and ensuing description.

What is claimed is:

1. A separator for separating solids from liquids by gravity comprising:

a manifold having an inlet conduit and an outlet conduit:

a baffle plate between said inlet and said outlet, said baffle plate having an internal conduit extending through said baffle plate; and a collection chamber below said manifold;

said baffle plate being adjustable between a first position wherein said baffle plate is interposed between said inlet and said outlet, wherein said baffle plate forms means for deflecting solids into said collection chamber; and a second position wherein said internal conduit is in communication with said inlet and said outlet, wherein said conduit forms means to bypass said collection chamber.

2. The separator according to claim 1 wherein said solids are heavy metals.

3. The separator according to claim 1 wherein said collection chamber is removable from said manifold.

4. The separator according to claim 1 wherein said baffle plate is adjustable using a control handle.

5. A separator for separating at least one heavy metal from non-heavy metal liquids by gravity comprising:

a manifold having an inlet conduit and an outlet conduit;

a baffle plate between said inlet and said outlet, said baffle plate having an internal conduit extending through said baffle plate; and a collection chamber below said manifold;

said baffle plate being adjustable between a first position wherein said baffle plate is interposed between said inlet and said outlet, wherein said baffle plate forms means for deflecting said heavy metal into said collection chamber; and a second position wherein said internal conduit is in communication with said inlet and said outlet, wherein said conduit forms means to bypass said collection chamber.

6. The separator according to claim 5 wherein said heavy metal is silver-mercury amalgam, silver, gold or mercury.

7. The separator according to claim 5 wherein said collection chamber is removable from said manifold.

8. The separator according to claim 5 wherein said baffle plate is adjustable using a control handle.

* * * * *

UNITED STATES PATENT AND TRADEMARK OFFICE
CERTIFICATE OF CORRECTION

PATENT NO. : 6,149,812      Page 1 of 1
DATED : November 21, 2000
INVENTOR(S) : Rodger E. Erickson It is certified that error appears in the above-identified patent and that said Letters Patent is hereby corrected as shown below:

<u>Column 3,</u>
Line 12, "fluids" should read -- solids --.
Line 48, "drawn" should read -- drawn by --.

Signed and Sealed this

Second Day of July, 2002

Attest:

Attesting Officer

JAMES E. ROGAN
*Director of the United States Patent and Trademark Office*